(12) United States Patent
Li et al.

(10) Patent No.: US 11,484,588 B1
(45) Date of Patent: Nov. 1, 2022

(54) PARAMYXOVIRUS VACCINE STRAIN FOR NOVEL CORONAVIRUS PNEUMONIA AND CONSTRUCTION METHOD THEREOF

(71) Applicant: QINGDAO HARWARS BIOLOGY GROUP LTD., Qingdao (CN)

(72) Inventors: Mingyi Li, Qingdao (CN); Gang Liu, Qingdao (CN); Chunlin Yi, Qingdao (CN); Fenglong Ma, Qingdao (CN); Zongke Wang, Qingdao (CN); Yujie Xia, Qingdao (CN); Xiaochen Cui, Qingdao (CN); Zhen Yang, Qingdao (CN); Hongshang Chang, Qingdao (CN); Bingbing Zhao, Qingdao (CN); Jie Yang, Qingdao (CN)

(73) Assignee: QINGDAO HARWARS BIOLOGY GROUP LTD., Qingdao (CN)

( * ) Notice: Subject to any disclaimer, the term of this patent is extended or adjusted under 35 U.S.C. 154(b) by 0 days.

(21) Appl. No.: 17/404,713

(22) Filed: Aug. 17, 2021

(30) Foreign Application Priority Data

Apr. 2, 2021  (CN) .......................... 202110361745.0

(51) Int. Cl.
| | |
|---|---|
| *A61K 39/215* | (2006.01) |
| *A61P 31/14* | (2006.01) |
| *A61P 11/00* | (2006.01) |
| *C12N 7/00* | (2006.01) |
| *A61K 39/00* | (2006.01) |

(52) U.S. Cl.
CPC ............ *A61K 39/215* (2013.01); *A61P 11/00* (2018.01); *A61P 31/14* (2018.01); *C12N 7/00* (2013.01); *A61K 2039/543* (2013.01); *C12N 2760/18121* (2013.01); *C12N 2760/18122* (2013.01); *C12N 2760/18144* (2013.01); *C12N 2760/18421* (2013.01); *C12N 2760/18422* (2013.01); *C12N 2760/18444* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

2020/0390883 A1   12/2020   Talaat

FOREIGN PATENT DOCUMENTS

| CN | 1620500 A | 5/2005 |
|---|---|---|
| CN | 111218459 B | 9/2020 |
| CN | 111840532 A | 10/2020 |
| CN | 112011521 A | 12/2020 |

OTHER PUBLICATIONS

NPL: "Establishment of BHK-21 cell lines stable expressing T7 Rna polymerase", Chinese Veterinary Science, 43(07):749-753, 2013.
Notice of Allowance of the parallel CN application No. 202110361745.0.

*Primary Examiner* — Nicole Kinsey White
(74) *Attorney, Agent, or Firm* — J.C. Patents (57) ABSTRACT

A paramyxovirus vaccine strain for novel coronavirus pneumonia and a construction method thereof are provided. The method includes performing a recombination of N and F genes of Newcastle disease virus type VII of Paramyxoviridae with P, M, H, L genes of Canine distemper virus of Paramyxoviridae to obtain a recombinant virus, inserting S1 gene of the novel coronavirus between the P and M genes of the recombinant virus to obtain a recombinant vector. The vaccine strain constructed can stably and efficiently express the novel coronavirus S1 protein, and induce the body to produce antibodies; and the recombined virus vaccine strain can stimulate the human body to produce mucosal immunity, and the prepared vaccine can be vaccinated through a nasal spray. Moreover, the vaccine strain can be tested in poultry and dogs, saving time, reducing costs, and being more conducive to actual production due to large output.

3 Claims, 4 Drawing Sheets

Specification includes a Sequence Listing.

SEQUENCE LISTING

```
<160> NUMBER OF SEQ ID NOS: 27

<210> SEQ ID NO 1
<211> LENGTH: 44
<212> TYPE: DNA
<213> ORGANISM: Artificial Sequence
<220> FEATURE:
<223> OTHER INFORMATION: Primer

<400> SEQUENCE: 1
ctgctcgagc caccatgaac acgattaaca tcgctaagaa cgac            44

<210> SEQ ID NO 2
<211> LENGTH: 41
<212> TYPE: DNA
<213> ORGANISM: Artificial Sequence
<220> FEATURE:
<223> OTHER INFORMATION: Primer

<400> SEQUENCE: 2
ctgtctagat tacgcgaacg cgaagtccga ctctaagatg t               41

<210> SEQ ID NO 3
<211> LENGTH: 47
<212> TYPE: DNA
<213> ORGANISM: Artificial Sequence
<220> FEATURE:
<223> OTHER INFORMATION: Primer

<400> SEQUENCE: 3
ggaattctaa tacgactcac tatagaccaa acagagaatc tgtgagg         47

<210> SEQ ID NO 4
<211> LENGTH: 42
<212> TYPE: DNA
<213> ORGANISM: Artificial Sequence
<220> FEATURE:
<223> OTHER INFORMATION: Primer

<400> SEQUENCE: 4
gtaacactgg tcttgaatat tcagtacccc caatcagtgt cg              42

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
cgacactgat tgggggtact gaatattcaa gaccagtgtt ac              42

<210> SEQ ID NO 6
<211> LENGTH: 32
```

-continued

<212> TYPE: DNA
<213> ORGANISM: Artificial Sequence
<220> FEATURE:
<223> OTHER INFORMATION: Primer

<400> SEQUENCE: 6
cgacgcgtcc gcgggatgat gcgggttgct tg					32

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
catcccgcgg taatcggaag g					21

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
cgacgcgtgc ccatggggct tgtctgttcg					30

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ccccatgggc tccaaacctt c					21

<210> SEQ ID NO 10
<211> LENGTH: 41
<212> TYPE: DNA
<213> ORGANISM: Artificial Sequence
<220> FEATURE:
<223> OTHER INFORMATION: Primer

<400> SEQUENCE: 10
gacgtgtgac cagattgctt catgctctcg tggtggctct c					41

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
gagagccacc acgagagcat gaagcaatct ggtcacacgt c					41

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12

```
cgacgcgtga taagcttgtc cagtgcatct c                                   31
```

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13

```
gacaagctta tcggggccaa aattg                                          25
```

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14

```
ctaaagcttc atcctcgtcc tg                                             22
```

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15

```
gaagctttag ccgctttctt gatg                                           24
```

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16

```
cgacgcgtct gctagcagat atctggctta g                                   31
```

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17

```
ctgctagcag tcttggattg attc                                           24
```

<210> SEQ ID NO 18
<211> LENGTH: 87
<212> TYPE: DNA
<213> ORGANISM: Artificial Sequence
<220> FEATURE:
<223> OTHER INFORMATION: Primer

<400> SEQUENCE: 18

```
cgacgcgtac gcgtcaaaaa acccctcaag acccgtttag aggccccaag gggttatgct    60
agaccagaca aagctgggta tgataac                                        87
```

<210> SEQ ID NO 19
<211> LENGTH: 32

<212> TYPE: DNA
<213> ORGANISM: Artificial Sequence
<220> FEATURE:
<223> OTHER INFORMATION: Primer

<400> SEQUENCE: 19
gctctagaat gtcgtctgtt ttcgacgaat ac                          32

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
tcccccgggt cagtaccccc aatcagtgtc                             30

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
gctctagaat ggcagaggag caggcctatc                             30

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
tcccccgggt cagtaccccc aatcagtgtc g                           31

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
gctctagaat ggacgccgtc tcagtgaac                              29

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
tcccccgggt cagtggtttc taatcagtgc                             30

<210> SEQ ID NO 25
<211> LENGTH: 2043
<212> TYPE: DNA
<213> ORGANISM: Novel coronavirus (2019-nCoV)

<400> SEQUENCE: 25
atgttcgtgt tcctggtgct gctgcctctg gtgagctccc agtgcgtgaa cctgaccacc    60

```
agaacccagc tgccacctgc ctacaccaac tcctttacca ggggcgtgta ttaccctgac    120
aaggtgttca gaagctccgt gctgcactcc acacaggacc tgttcctgcc attcttttcc    180
aacgtgactt ggttccacgc catccatgtg tctggcacca atggcacaaa gaggtttgac    240
aatccagtgc tgccttttcaa tgacggcgtg tattttgcct ccacagagaa gtctaatatc    300
atcagaggct ggatcttcgg cacaaccctg gattctaaga cccagtccct gctgatcgtg    360
aataatgcca ccaacgtcgt gatcaaggtg tgtgagtttc agttctgcaa cgacccttc     420
ctgggcgtgt actaccacaa gaataacaag tcttggatgg agtctgagtt ccgggtgtac    480
tctagcgcta ataactgtac cttcgagtac gtgagccagc cctttctgat ggacctggag    540
ggcaagcagg ggaactttaa gaacctgagg gagttcgtgt tcaagaacat tgacggctac    600
tttaagatct attctaagca cacaccaatc aacctggtga gggatctgcc tcagggcttc    660
tccgccctgg agcccctggt ggacctgcct atcggcatca acatcaccag attccagacc    720
ctgctcgctc tgcatagaag ctacctgacc cccggcgaca gctcttccgg atggaccgct    780
ggcgctgccg cctactacgt gggctacctg cagcccggga ccttcctgct gaagtacaat    840
gagaacggaa ccatcaccga cgccgtggac tgtgctctgg accccctgag cgagaccaag    900
tgcactctga agtccttcac cgtggagaag ggcatctacc agacttctaa ctttcgggtg    960
cagcctaccg agtccattgt gcggttccct aacatcacta atctgtgccc attcggcgag   1020
gtgtttaacg ccacccggtt cgctagcgtg tacgcctgga acaggaagcg catctccaac   1080
tgtgtggccg actactctgt gctgtacaat tctgccagct tttctacctt caagtgttac   1140
ggcgtgagcc caacaaaact gaacgacctg tgctttacca acgtgtacgc cgacagcttc   1200
gtgatcaggg gcgatgaggt gagacagatc gcccctggcc agaccggcaa gatcgccgac   1260
tataactaca agctgcctga tgatttcacc ggatgcgtga tcgcctggaa ctctaacaat   1320
ctggatagca aggtgggcgg gaattacaac tacctgtaca gactgttcag aaagtccaac   1380
ctgaagccct tcgagcggga catctccacc gagatctacc aggctggatc aaccccctgc   1440
aacggcgtgg agggctttaa ttgttacttt ccctgcagt cttacggctt ccagcccacc   1500
aacggcgtgg gctaccagcc ttatagagtg gtggtgctga gctttgagct gctgcacgcc   1560
cctgccaccg tgtgcggccc taagaagtct acaaacctgg tgaagaataa gtgcgtgaac   1620
tttaatttca acggcctgac cggcaccggc gtgctgaccg agagcaacaa gaagttcctg   1680
cccttccagc agttcggaag ggacatcgcc gatacaaccg acgccgtgag agacccacag   1740
acccctggaga tcctggacat cacccccttgt agctttggcg gcgtgagcgt gatcacccct   1800
ggcaccaaca cctccaacca ggtggccgtg ctgtaccagg acgtgaattg cactgaggtg   1860
cctgtggcta tccacgctga ccagctgacc cctacctgga gagtgtatag caccggatcc   1920
aacgtgttcc agaccagagc tggctgcctg atcggcgctg agcacgtgaa taacagctat   1980
gagtgtgaca tccccatcgg cgccggcatc tgcgctagct accagaccca gaccaactcc   2040
tga                                                                 2043
```

<210> SEQ ID NO 26
<211> LENGTH: 41
<212> TYPE: DNA
<213> ORGANISM: Artificial Sequence
<220> FEATURE:
<223> OTHER INFORMATION: Primer

<400> SEQUENCE: 26
gaactgcttt caccatcgtt taaacttaag aaaaaacacg g                       41

```
<210> SEQ ID NO 27
<211> LENGTH: 45
<212> TYPE: DNA
<213> ORGANISM: Artificial Sequence
<220> FEATURE:
<223> OTHER INFORMATION: Primer

<400> SEQUENCE: 27
ctaagttttt tataattgcg tttaaacggg tcaggagttg gtctg            45
```

PARAMYXOVIRUS VACCINE STRAIN FOR NOVEL CORONAVIRUS PNEUMONIA AND CONSTRUCTION METHOD THEREOF

CROSS-REFERENCE TO RELATED APPLICATION

This application claims priority to Chinese Patent Application No. 202110361745.0, filed on Apr. 2, 2021, which is hereby incorporated by reference in its entirety.

TECHNICAL FIELD

The present application belongs to the technical field of new biomedicine engineering, and specifically relates to a paramyxovirus vaccine strain for novel coronavirus pneumonia (CoV) and a construction method thereof.

BACKGROUND

Since 2019, novel coronavirus has raged and spread widely around the world, causing a large number of casualties. Although novel coronavirus vaccines are currently available, they have relatively low output and are far from being able to meet the needs of the market. At the same time, immunization methods for the vaccines are all injection immunization, and there is no nasal injection immunization product on the market. Current studies have shown that a novel coronavirus spike (S) protein plays an important role in virus infection and induction of the production of neutralizing antibodies.

SUMMARY

An object of the present disclosure is to provide a paramyxovirus vaccine strain for novel coronavirus pneumonia and its construction method. The paramyxovirus vaccine strain for novel coronavirus pneumonia can stimulate the body to produce a high-titer specific anti-SAR-CoV-2 (severe acute respiratory syndrome coronavirus 2) neutralizing antibody through nasal spray, so as to prevent pneumonia infections due to novel coronavirus.

In order to achieve the above object, the present disclosure adopts the following technical solutions:

According to one aspect of the present disclosure, there is provided a paramyxovirus vaccine strain for novel coronavirus pneumonia, where the paramyxovirus vaccine strain for novel coronavirus pneumonia is a recombinant paramyxovirus strain that expresses novel coronavirus S1 protein (rCNDV-S), with an access number CCTCC NO: V202119, deposited in China Center for Type Culture Collection, Wuhan University, Wuhan, China.

According to another aspect of the present disclosure, there is provided a vaccine composition, including a pharmaceutically effective amount of the paramyxovirus vaccine strain for novel coronavirus pneumonia above and a pharmaceutically acceptable adjuvant.

In an embodiment of the present disclosure, the pharmaceutically acceptable adjuvant is one or more selected from the group consisting of propolis, liposomes, lentinan, *ganoderma* polysaccharide, *astragalus* polysaccharide, *gastrodia* extract, *cordyceps* extract, *Sophora flavescens* extract, and levamisole.

According to another aspect of the present disclosure, there is provided use of the above paramyxovirus vaccine strain for novel coronavirus pneumonia or the above vaccine composition in preparation of a vaccine for novel coronavirus pneumonia.

In an embodiment of the present application, the vaccine for novel coronavirus pneumonia is administered for immunization by nasal spray.

In an embodiment of the present disclosure, the vaccine for novel coronavirus pneumonia can stimulate the body to produce specific neutralizing antibody against SARS-CoV-2.

In an embodiment of the present disclosure, the vaccine for novel coronavirus pneumonia is used to prevent diseases or conditions caused by the novel coronavirus.

In an embodiment of the present disclosure, the vaccine for novel coronavirus pneumonia is in the form of a spray.

According to another aspect of the present disclosure, there is provided use of the aforementioned paramyxovirus vaccine strain for novel coronavirus pneumonia or the above vaccine composition in the prevention of diseases or conditions caused by the novel coronavirus.

In an embodiment of the present disclosure, the diseases or conditions include: fever, dry cough, and fatigue.

According to another aspect of the present disclosure, there is provided a method for preventing novel coronavirus pneumonia caused by SARS-CoV-2, including: administering the paramyxovirus vaccine strain for novel coronavirus pneumonia according to the present disclosure to a subject in the form of a vaccine composition, prior to the subject being infected with novel coronavirus pneumonia.

In an embodiment of the present disclosure, an effective administration concentration of the paramyxovirus vaccine strain for novel coronavirus pneumonia is $10^{5.0} \sim 10^{6.5}$ $TCID_{50}$/0.1 ml.

According to yet another aspect of the present disclosure, there is provided a method for constructing a paramyxovirus vaccine strain for novel coronavirus pneumonia, including the steps of: performing a recombination of N and F genes of Newcastle disease virus (NDV) type VII with P, M, H, L genes of Canine distemper virus (CDV) to obtain a recombinant virus, and inserting S1 gene of the novel coronavirus between the P and M genes of the recombinant virus, to obtain a recombinant paramyxovirus vector expressing the S1 gene of novel coronavirus, where the paramyxovirus vaccine strain for novel coronavirus pneumonia is as described above.

In an embodiment of the present disclosure, the paramyxovirus vaccine strain for novel coronavirus pneumonia is constructed by a reverse genetic manipulation, where the reverse genetic manipulation is as follows: co-transfecting a cell line capable of expressing T7 RNA polymerase with both the constructed a recombinant paramyxovirus vector expressing the S1 gene of novel coronavirus and three auxiliary recombination plasmids respectively containing NP, P, and L genes; and incubating to obtain a paramyxovirus vaccine strain for novel coronavirus pneumonia.

In an embodiment of the present disclosure, the cell line capable of expressing T7 RNA polymerase is obtained by coupling T7 RNA polymerase genes with a pCI-neo vector and then transfecting into BHK-21 cells.

The vaccine composition described above has a preventive and protective effect on the novel coronavirus pneumonia caused by SARS-CoV-2.

Advantages of the technical solution of the present disclosure are as follows:

In the present disclosure, the S1 gene of the novel coronavirus is inserted into a recombinant virus vector, and the constructed paramyxovirus vaccine strain for novel coronavirus pneumonia is capable of stably and efficiently expressing S1 protein of the novel coronavirus, and inducing the body immunized to produce high-titer neutralizing antibodies. Such paramyxovirus vaccine strain for novel coronavirus pneumonia can be propagated and cultured in mammalian cells or 9-11-day-old SPF chicken embryos, and has the advantages of simple operation, low cost, large yield and the like. Moreover, the vaccine strain can also be tested in poultry and dogs, which can save time and reduce costs.

In addition, existing poxvirus and adenovirus vectors have pre-existing immunity and the neurophilicity of herpes virus may cause safety problems. The canine distemper virus used in the present disclosure belongs to virus of Morbillivirus, Paramyxoviridae, and is infective to mammalian cells but not pathogenic to humans. The canine distemper virus can stably express foreign proteins and has almost no gene mutation phenomenon under non-human circumstances, and thus it is a good vaccine vector. The Newcastle disease virus belongs to the Paramyxoviridae virus, and can be propagated and cultured in mammalian cells or 9-11-day-old chicken embryos, and has the advantages of simple operation, low cost, large yield, and the like. Finally, the vaccine strain constructed by the method of the present disclosure can be replicated in cytoplasm and will not be integrated into a host genome, and the virus vector hardly undergoes genetic mutations, and has high safety.

DESCRIPTION OF EMBODIMENTS

Unless otherwise specified, the terms used in the present disclosure generally have the meanings commonly understood by those of ordinary skill in the art.

The present disclosure will be described in further detail below in conjunction with specific examples and with reference to data. The following examples are only to illustrate the present disclosure, but not to limit the scope of the present disclosure in any way.

Example 1 Construction Method of Paramyxovirus Vaccine Strain for Novel Coronavirus Pneumonia (1) Establishment of Cell Line Expressing T7 RNA Polymerase (BHK21-T7)

BL21 strain was taken and shaken to prepare DNA, from which the T7 RNA polymerase gene fragment is amplified and obtained by PCR. Primers (the underlined indicated enzyme cutting site) are designed as follows:

(SEQ ID NO: 1)
T7-F: 5'-CTGCTCGAGCCACCATGAACACGATTAACATCGCT
AAGAACGAC-3';
and (SEQ ID NO: 2)
T7-R: 5'-CTGTCTAGATTACGCGAACGCGAAGTCCGACTCTA
AGATGT-3';

The enzyme cutting sites were: upstream Xho I, and downstream Xba I (marked by the underline). The extracted BL21 DNA was used as a template for amplification and a target fragment was recovered, about 2.6 kb. The recovered target fragment and pCI-neo vector plasmid were subjected to double enzyme digestion with Xho I/Xba I respectively, and the target fragment was recovered by agarose gel electrophoresis, ligated with T4 ligase and transformed into DH5α competent cells. Plasmids were extracted in a small amount and identified by PCR and restriction enzyme digestion. Positive plasmids were selected for sequencing. If the sequence of the positive plasmids was proved to be correct a large number of recombinant plasmids containing the T7 RNA polymerase gene were prepared.

BHK-21 cells were cultured with DMEM containing 6% fetal bovine serum (Gibco) and inoculated with a 6-well plate. When the BHK-21 cells grew to about 70%, the cells were transfected with the prepared recombinant plasmid carrying the T7 RAN polymerase gene according to instructions of a liposome transfection kit (Invitrogen: 11668027). After 24 hours of transfection, the culture medium was replaced with DMEM containing G418 (700 ng/mL) for pressure screening. Cell RNA was extracted when the screened cells were passed continuously to the 25th generation, and then RT-PCR identification was performed after reverse transcription. Finally, the BHK-21 cell line (BHK21-T7) that can stably and continuously express the T7 RNA polymerase gene was obtained.

(2) Construction of Recombinant Expression Vector pBR322-CDV-NPF

The RNAs of CDV and NDV type VII were extracted, primers were designed for RT-PCR, and a whole genome sequence of a recombinant virus was constructed by enzyme digestion and homologous recombination. The whole genome sequence of the recombinant virus was divided into 8 segments for cloning, and the primers were as follows (the underline indicated the enzyme cutting site):

1-F:

(SEQ ID NO: 3)
1-F: 5'-GGAATTCTAATACGACTCACTATAGACCAAACAGAGAAT
CTGTGAGG-3';

(SEQ ID NO: 4)
1-R: 5'-GTAACACTGGTCTTGAATATTCAGTACCCCCAATCA
GTGTCG-3';

(SEQ ID NO: 5)
2-F: 5'-CGACACTGATTGGGGGTACTGAATATTCAAGACCAG
TGTTAC-3;

(SEQ ID NO: 6)
2-R: 5'-CGACGCGTCCGCGGGATGATGCGGGTTGCTTG-3';

(SEQ ID NO: 7)
3-F: 5'-CATCCCGCGGTAATCGGAAGG-3';

(SEQ ID NO: 8)
3-R: 5'-CGACGCGTGCCCATGGGGCTTGTCTGTTCG-3';

-continued

```
                                         (SEQ ID NO: 9)
4-F: 5'-CCCCATGGGCTCCAAACCTTC-3';

(SEQ ID NO: 10)
4-R: 5'-GACGTGTGACCAGATTGCTTCATGCTCTCGTGGTG
GCTCTC-3';

(SEQ ID NO: 11)
5-F: 5'-GAGAGCCACCACGAGAGCATGAAGCAATCTGGTC
ACACGTC-3';

(SEQ ID NO: 12)
5-R: 5'-CGACGCGTGATAAGCTTGTCCAGTGCATCTC-3';

(SEQ ID NO: 13)
6-F: 5'-GACAAGCTTATCGGGGCCAAAATTG-3';

(SEQ ID NO: 14)
6-R: 5'-CTAAAGCTTCATCCTCGTCCTG-3';

(SEQ ID NO: 15)
7-F: 5'-GAAGCTTTAGCCGCTTTCTTGATG-3';

(SEQ ID NO: 16)
7-R: 5'-CGACGCGTCTGCTAGCAGATATCTGGCTTAG-3';

(SEQ ID NO: 17)
8-F: 5'-CTGCTAGCAGTCTTGGATTGATTC-3';

(SEQ ID NO: 18)
8-R: 5'-CGACGCGTACGCGTCAAAAAACCCCTCAAGACCCGTT
TAGAGGCCCCAAGGGGTTATGCTAGACCAGACAAAGCTGGGTATG
ATAAC-3'.
```

Among them, the first segment (1-F, 1-R) and the fourth segment (4-F, 4-R) primers were amplified using NDV type VII as a template; the rest segments were amplified using CDV as a template. After the amplification was completed, each fragment was recovered by agarose gel electrophoresis, and the whole genome sequence of the recombinant virus was constructed from sequences of fragments by enzyme digestion and homologous recombination. Furthermore, a promotor sequence of T7 was added upstream of the whole genome sequence and a terminator sequence of T7 was added downstream thereof, and a pBR322 vector was introduced to construct a recombinant plasmid pBR322-CDV-NPF.

(3) Construction of Auxiliary Plasmid

The pBR322-CDV-NPF plasmid constructed above was used as a template to clone the NP, P, and L genes, respectively. PCR primers for each gene are as follows (the underline indicated the enzyme cutting site):

```
                                         (SEQ ID NO: 19)
NP-F: 5'-GCTCTAGAATGTCGTCTGTTTTCGACGAATAC-3';

(SEQ ID NO: 20)
NP-R: 5'-TCCCCCGGGTCAGTACCCCCAATCAGTGTC-3';

(SEQ ID NO: 21)
P-F: 5'-GCTCTAGAATGGCAGAGGAGCAGGCCTATC-3';

(SEQ ID NO: 22)
P-R: 5'-TCCCCCGGGTCAGTACCCCCAATCAGTGTCG-3';

(SEQ ID NO: 23)
L-F: 5'-GCTCTAGAATGGACGCCGTCTCAGTGAAC-3';

(SEQ ID NO: 24)
L-R: 5'-TCCCCCGGGTCAGTGGTTTCTAATCAGTGC-3';
```

PCR products recovered by agarose gel electrophoresis and pCI-neo plasmid were subjected to double enzyme digestion with Xba I/Sma I respectively, and the digested products were recovered. The digested products were ligated by T4 DNA ligase at 16° C. for 4 hours. The ligated products were transformed into XL-10 chemocompetent cells, incubating overnight at 37° C. A single clone was picked up and inoculated in a liquid medium containing ampicillin, incubating overnight at 37° C. and 220 rpm. A single colony was identified by PCR, and the positive clones were sequenced and analyzed by the Illumina NextSeq 500 system to obtain target plasmids, which were named as pCI-neo-NP, pCI-neo-P, and pCI-neo-L respectively.

(4) Construction of the Whole Genome Recombinant Vector of the Novel Coronavirus Pneumonia Paramyxovirus According to the SARS-CoV-2-S1 gene sequence MN908947.3 published in Genbank, a pUC57 plasmid containing the SARS-CoV-2 S1 protein encoding gene was synthesized by Shanghai Shenggong Biotechnology Co., Ltd., where the nucleotide sequence of SARS-CoV-2 S1 gene is SEQ ID NO: 25.

```
                                                    (SEQ ID NO: 25)
        atgttcgtgt tcctggtgct gctgcctctg gtgagctccc agtgcgtgaa cctgaccacc      60
agaacccagc tgccacctgc ctacaccaac tcctttacca ggggcgtgta ttaccctgac     120
aaggtgttca gaagctccgt gctgcactcc acacaggacc tgttcctgcc attcttttcc     180
aacgtgactt ggttccacgc catccatgtg tctggcacca atggcacaaa gaggtttgac     240
aatccagtgc tgcctttcaa tgacggcgtg tattttgcct ccacagagaa gtctaatatc     300
atcagaggct ggatcttcgg cacaaccctg gattctaaga cccagtccct gctgatcgtg     360
aataatgcca ccaacgtcgt gatcaaggtg tgtgagtttc agttctgcaa cgacccttc      420 ctgggcgtgt actaccacaa gaataacaag tcttggatgg agtctgagtt ccgggtgtac     480
tctagcgcta ataactgtac cttcgagtac gtgagccagc cctttctgat ggacctggag     540
ggcaagcagg gaactttaa  gaacctgagg gagttcgtgt tcaagaacat tgacggctac     600
tttaagatct attctaagca cacaccaatc aacctggtga gggatctgcc tcagggcttc     660
tccgccctgg agccctggt  ggacctgcct atcggcatca acatcaccag attccagacc     720
ctgctcgctc tgcatagaag ctacctgacc cccggcgaca gctcttccgg atggaccgct     780
```

```
ggcgctgccg cctactacgt gggctacctg cagccccgga ccttcctgct gaagtacaat      840
gagaacggaa ccatcaccga cgccgtggac tgtgctctgg acccoctgag cgagaccaag      900 tgcactctga agtccttcac cgtggagaag ggcatctacc agacttctaa ctttcgggtg      960
cagcctaccg agtccattgt gcggttccct aacatcacta atctgtgccc attcggcgag     1020
gtgtttaacg ccacccggtt cgctagcgtg tacgcctgga acaggaagcg catctccaac     1080
tgtgtggccg actactctgt gctgtacaat tctgccagct tttctacctt caagtgttac     1140
ggcgtgagcc aacaaaact gaacgacctg tgctttacca acgtgtacgc cgacagcttc     1200
gtgatcaggg gcgatgaggt gagacagatc gcccctggcc agaccggcaa gatcgccgac     1260
tataactaca agctgcctga tgatttcacc ggatgcgtga tcgcctggaa ctctaacaat     1320
ctggatagca aggtgggcgg gaattacaac tacctgtaca gactgttcag aaagtccaac     1380
ctgaagcctt tcgagcggga catctccacc gagatctacc aggctggatc aaccccctgc     1440
aacggcgtgg agggctttaa ttgttacttt cccctgcagt cttacggctt ccagcccacc     1500
aacggcgtgg gctaccagcc ttatagagtg gtggtgctga gctttgagct gctgcacgcc     1560
cctgccaccg tgtgcggccc taagaagtct acaaacctgg tgaagaataa gtgcgtgaac     1620
tttaatttca acggcctgac cggcaccggc gtgctgaccg agagcaacaa gaagttcctg     1680
cccttccagc agttcggaag ggacatcgcc gatacaaccg acgccgtgag agacccacag     1740
accctggaga tcctggacat cacccottgt agctttggcg gcgtgagcgt gatcaccoct     1800 ggcaccaaca cctccaacca ggtggccgtg ctgtaccagg acgtgaattg cactgaggtg     1860
cctgtggcta tccacgctga ccagctgacc cctacctgga gagtgtatag caccggatcc     1920
aacgtgttcc agaccagagc tggctgcctg atcggcgctg agcacgtgaa taacagctat     1980
gagtgtgaca tccccatcgg cgccggcatc tgcgctagct accagaccca gaccaactcc     2040
tga                                                                    2043
```

Figure 1:
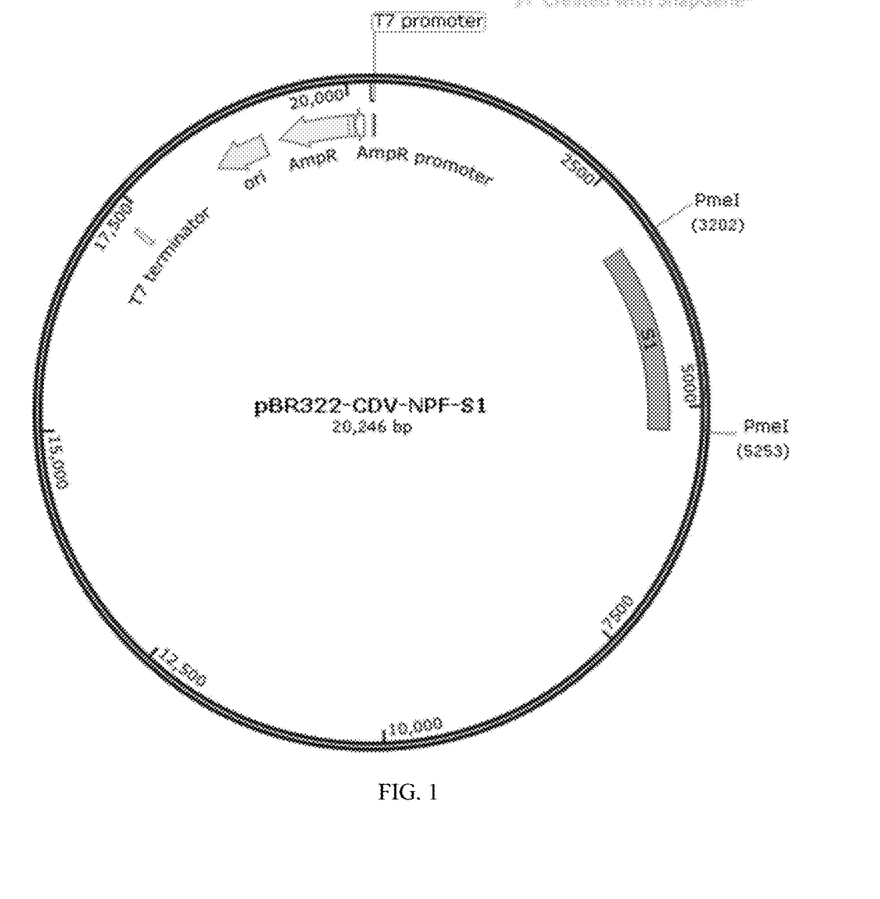
FIG. 1 shows a map of pBR322-CDV-NPF-S1 vector plasmid.

A specific procedure included the following steps:

according to the SARS-CoV-2 S1 protein coding sequence of SEQ ID NO: 25, designing the amplification primers using a pUC57 cloning vector containing the sequence as a template, where the primer sequences were as follows:

nCoV2019-S1-F:

```
                                                      (SEQ ID NO: 26)
nCoV2009-S1-F: 5'-GTTTAAACTTAAGAAAAAACAC
GGGTAGAAATGTTCGTGTTCCTGGTGC-3';

(SEQ ID NO: 27)
nCoV2019-S1-R: 5'-GTTTAAACTCAGGAGTTGGTCTGG
GTC-3';
``` and performing PCR amplification of SARS-CoV-2 S1 gene according to the following procedure: pre-denaturing at 98° C. for 2 min; 30 cycles (denaturing at 98° C. for 10 s; annealing at 60° C. for 30 s; extending at 72° C. for 2 min); and extending at 72° C. for 10 min. The gel containing positive fragments identified by agarose (1%) gel electrophoresis were recovered and purified to obtain the SARS-CoV-2 S1 gene fragment. The pBR322-CDV-NPF vector was subjected to single enzyme digestion with Pme I and was ligated with the SARS-CoV-2 S1 gene fragment at 16° C. overnight. The ligated product was transformed into XL-10 chemocompetent cells and incubated at 37° C. overnight. A single clone was picked up and inoculated in a liquid medium containing ampicillin at 37° C. and at 220 rpm overnight. A single colony was identified by PCR, and the positive clones were sequenced and analyzed by the Illumina NextSeq 500 system to obtain an expression vector plasmid correctly ligated with S1 gene, where the expression vector plasmid is named as pBR322-CDV-NPF-S1, as shown in FIG. 1.

(5) Cell Transfection and Virus Rescue

The plasmid pBR322-CDV-NPF-S1 constructed in step (4) and the auxiliary plasmids pCI-neo-NP, pCI-neo-P, and pCI-neo-L constructed in step (3) were transferred into the cultured BHK21-T7 cells by liposome transfection. After culturing for 48-72 hours, the cells and cell supernatant were collected, and were frozen and thawed once at −20° C. The supernatant was collected aseptically after centrifugation and filtered at 0.22 μm to obtain a filtrate. The filtrate was inoculated aseptically into 9-11-day-old SPF chicken embryos, and continued to incubate for 2-4 days. An allantoic fluid was collected aseptically and tested for its hemagglutination (HA) titer. Through RT-PCR identification and sequence analysis, an allantoic fluid containing SARS-CoV-2-S1 protein and having a hemagglutination titer 7-8 log 2, RT-PCR positive and correct sequence, was obtained, indicating that the virus rescue was successful.

The above-mentioned successfully rescued virus was deposited in the China Type Culture Collection, Wuhan University, Wuhan, China, on Feb. 11, 2021, with a deposit number of CCTCC NO: V202119 and a deposit name of a recombinant paramyxovirus strain expressing novel coronavirus S1 Protein (rCNDV-S).

Figure 2:
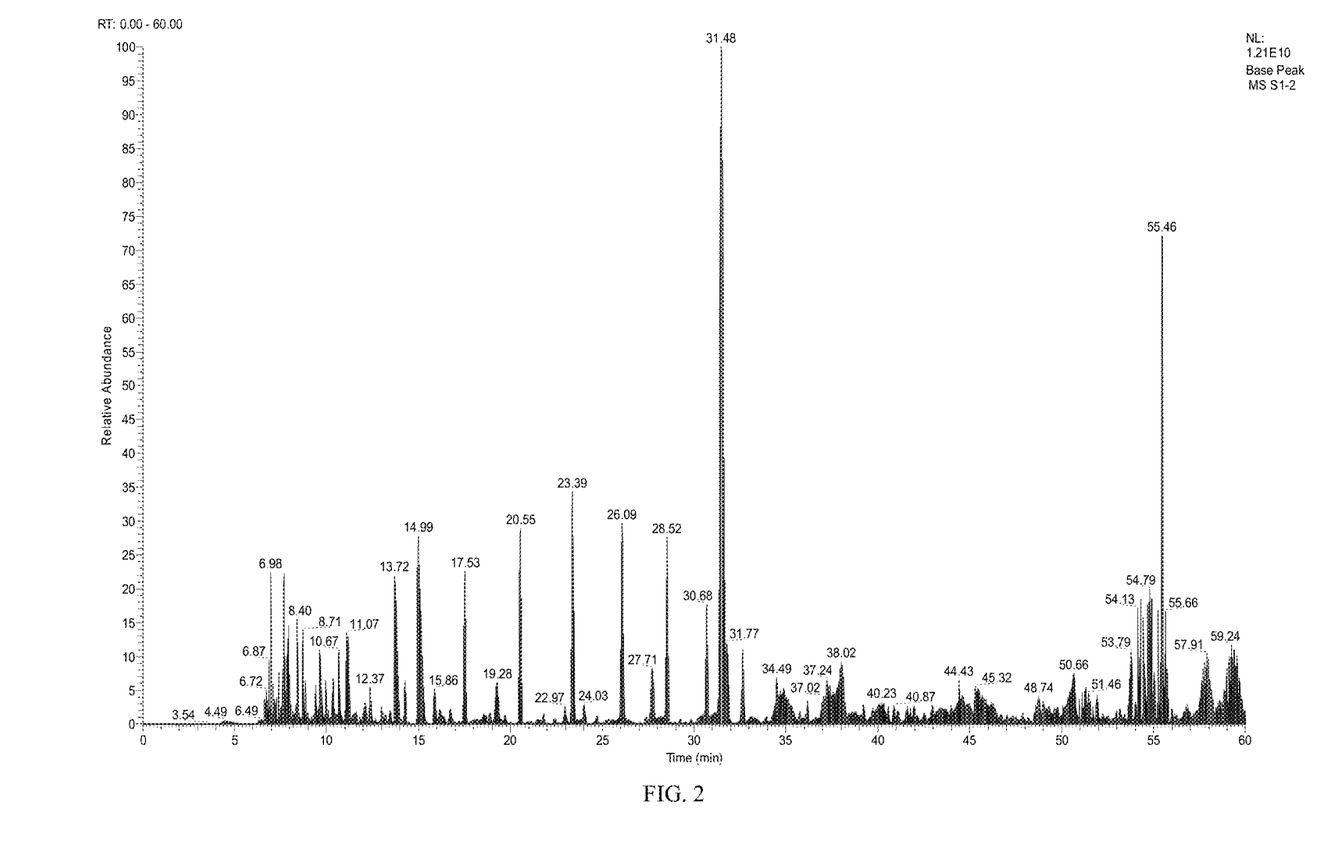
FIG. 2 shows a mass spectrometry analysis of S1 protein expressed by the paramyxovirus vaccine strain for novel coronavirus pneumonia.

Example 2 Expression and Biological Activity Identification of S1 Protein of Paramyxovirus Vaccine Strain for Novel Coronavirus Pneumonia Liquid Chromatography Tandem Mass Spectrometry (LC-MS/MS) Analysis The LC-MS/MS analysis was performed by the following steps: after enzymatic hydrolysis of each sample, an appropriate amount of enzymatically hydrolyzed peptide segments were taken and subjected to chromatographic separation through a nanoliter flow rate Easy nLC 1200 chromatography system (Thermo Scientific), wherein a buffer solution includes solution A: 0.1% of formic acid in water, and solution B: 0.1% of formic acid and 80% of acetonitrile in water. The column was balanced with 100% of the solution A. The sample was injected into the Trap Column (100 μm×20 mm, 5 μm, C18, Dr. Maisch GmbH) and then passed through a chromatographic analysis column (75 μm*150 mm, 3 μm, C18, Dr. Maisch GmbH) for gradient separation at a flow rate of 300 nl/min. A liquid phase separation gradient was used as follows: 0-2 min, solution B with a linear gradient from 2% to 5%; 2-44 min, solution B with a linear gradient from 5% to 28%; 44-51 min, solution B with a linear gradient from 28% to 40%; 51-53 min, solution B with a linear gradient from 40%-100%; and 53-60 min, solution B of 100%. After separation of the peptide segments, the Q-Exactive HF-X mass spectrometer (Thermo Scientific) was used for DDA mass spectrometry analysis, where analysis time: 60 min; detection mode: positive ion; parent ion scan range: 350-1800 m/z; resolution of primary mass spectrometer: 60,000 @m/z 200; AGC target: 3e6; primary maximum IT: 50 ms. Secondary mass spectrometry analysis of peptide segments was performed according to the following method: after each full scan, a secondary mass spectrum of 20 highest-intensity parent ions was triggered and collected (MS2 scan), where resolution of the secondary mass spectrum: 15,000@ m/z 200; AGC target: 1e5; Level 2 Maximum IT: 50 ms; MS2 Activation Type: HCD; Isolation window: 1.6 m/z; Normalized collision energy: 28. After searching and analyzing via MaxQuant 1.6.1.0, the results showed that: LC-MS/MS mass spectrometry analysis showed specific peptide segments, and the mass spectrometry results were as shown in FIG. 2. It showed that the SARS-CoV-2 S1 gene was expressed in recombinant cells of BHK21-T7/pBR322-CDV-NPF-S1.

Figure 3:
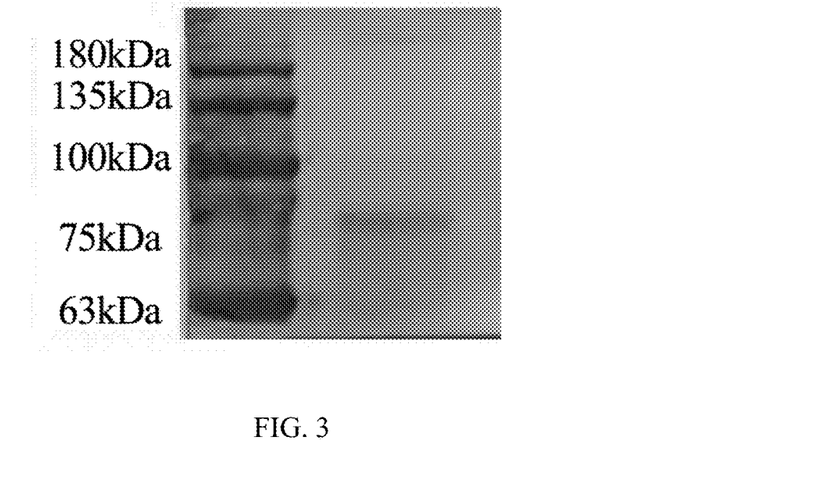
FIG. 3 shows Western Blot (WB) identification of S1 protein expressed by the paramyxovirus vaccine strain for novel coronavirus pneumonia.

Western Blot (WB) Identification:

The culture supernatant of the constructed recombinant cells, containing the SARS-CoV-2 S1 protein gene, of BHK21-T7/pBR322-CDV-NPF-S1 was subjected to Western Blot analysis and LC-MS/MS analysis. The Western Blot analysis step includes: SDS-PAGE gel electrophoresis was performed on a sample group, a control group and a protein marker, the electrophoresis was stopped when the bromophenol blue dye moved to the end of the gel, and the protein was transferred from the gel to a nitrocellulose membrane. After transferring to the membrane, it is blocked with a skimmed milk powder for 1 hour. An appropriate amount of mouse anti-SARS-CoV-2 S1 protein monoclonal antibody was added as a primary antibody for reaction, followed by incubating at 37° C. for 1 hour, and washing with TBST for 4 times. A FITC-labeled goat anti-mouse IgG secondary antibody was then added for reaction, followed by incubating at 37° C. for 1 hour, washing with TBST for 4 times, then adding a luminescent substrate solution for developing. WB results showed that the supernatant control group of empty vector cells showed no band, while the sample group had obvious bands, as shown in FIG. 3.

Figure 4:
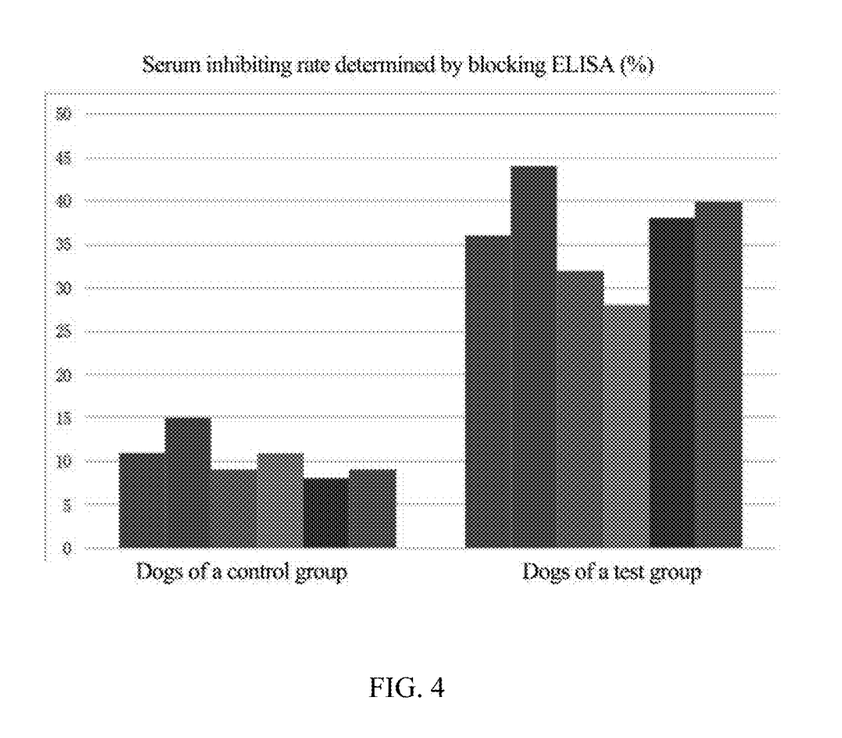
FIG. 4 shows a level analysis of anti-SARS-CoV-2 neutralizing antibody in the serum of Beagle dogs.

Example 3 Animal Immunogenicity of Paramyxovirus Vaccine Strain for Novel Coronavirus Pneumonia (1) 12 1-month-old beagle dogs were taken and randomly divided into a control groups and a test group, with 6 dogs in each group. The control group was immunized by nasal spray with sterile normal saline, and the test group was immunized by nasal spray with a sample vaccine of $10^{8.3}$ $EID_{50}$/0.1 ml prepared from rCNDV-S virus cultured in SPF chicken embryo, once a day, 200 μl every time, continuous immunization for 3 days. On the 14th day (D14) after immunization, blood was collected from the forelimb veins of dogs in the control and test groups, for separating serum. The level of the neutralizing antibody was determined by blocking ELISA. As shown in FIG. 4, only dogs in the test group produced specific antibodies, and the antibody level was significantly higher than that in the control group ($P<0.05$). It showed that rCNDV-S virus cultured from the allantoic fluid of chicken embryo can be used as an antigen to prepare a novel coronavirus vaccine, and the beagle dogs can be immunostimulated by nasal spray to produce specific antibodies.

Figure 5:
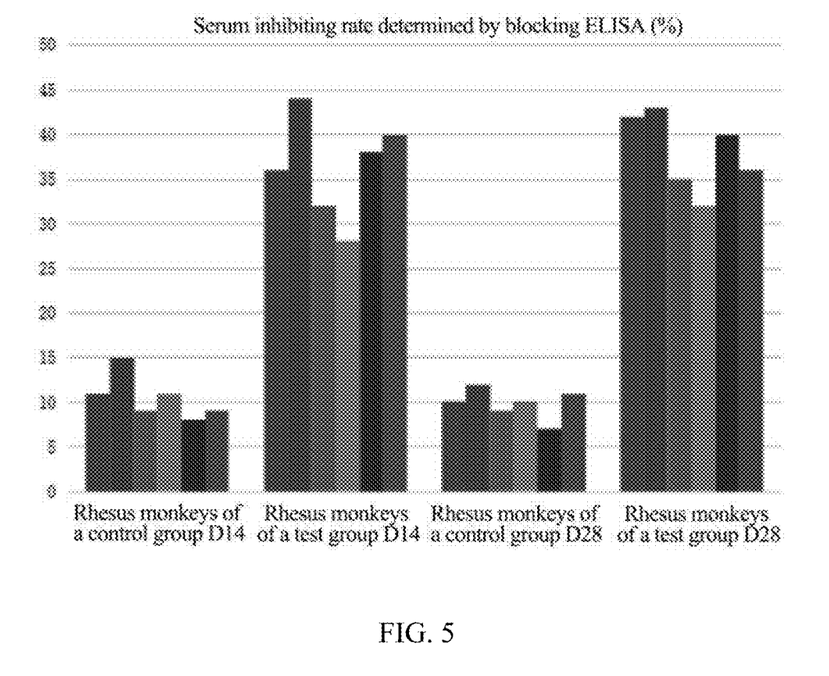
FIG. 5 shows a level analysis of anti-SARS-CoV-2 neutralizing antibody in the serum of rhesus monkey.

(2) 12 experimental rhesus monkeys of 3-4 kg were taken and divided into a control group and a test group randomly, with 6 animals in each group. The control group was immunized by nasal spray with sterile normal saline, and the test group was immunized by nasal spray with a sample vaccine of $10^{8.3}$ $EID_{50}$/0.1 ml prepared from rCNDV-S virus cultured in SPF chicken embryo, once a day, 200μl every time, continuous immunization for 3 days. On the 14th day (D14) and 28th day (D28), blood was collected from the forelimb veins of all experimental rhesus monkeys for separating serum. The level of the neutralizing antibody was determined by blocking ELISA. As shown in FIG. 5, only rhesus monkeys in the test group produced specific antibodies, and the level of the antibody was significantly higher than that in the control group ($P<0.05$). It showed that rCNDV-S virus cultured from the SPF chicken embryo can be used as an antigen to prepare a novel coronavirus vaccine, and the rhesus monkeys can be immunestimulated by nasal spray to produce specific antibodies.

Example 4 Stability of Paramyxovirus Vaccine Strain for Novel Coronavirus Pneumonia The lung tissues of the New Zealand white rabbits immunized with the method in Example 3 were ground and diluted with normal saline to obtain diluted tissue solution. Another five healthy New Zealand white rabbits were randomly selected to inoculate with the diluted tissue solution of 100 μL for each rabbit, numbered as Nos. 1-5. After 7 days, the lung tissues of rabbits Nos. 1-5 were ground and diluted with normal saline, and underwent aseptic treatment, to randomly inoculate another 5 healthy rabbits, numbered as Nos. 6-10. In such way, the lung tissues of rabbits Nos. 25-30 were ground and diluted with normal saline, to inoculate the last 5 healthy rabbits, numbered as Nos. 31-35. All the 7 groups of rabbits were tested for recombinant virus. Meanwhile, RNA was extracted and reverse transcribed into cDNA, and S1 gene was amplified by RT-PCR. If there was a positive gene, it would be sent to Shanghai Shenggong Biotechnology Co., Ltd. for sequencing.

Stability test of the vaccine strain using Beagle dogs as an animal model was the same as above.

Experimental results: recombinant virus can be detected in 35 rabbits and 35 beagle dogs in animal stability test. By analyzing and comparing of the sequence, it was found that the sequencing results of the S1 gene was the same as the S1 gene sequence which was inserted into the vector, indicating that the recombinant virus has not undergone mutations, the passage is stable, and there was no the virulence enhancement of virus.

The above are only preferred examples of the present disclosure, and are not intended to limit the present disclosure in other forms. Any person familiar with the profession may use the technical content disclosed above to make a change or modification to obtain the equivalent examples. However, without departing from the content of the technical solution of the present disclosure, any simple modifications, and equivalent changes and modifications made to the above examples based on the technical essence of the present disclosure still belong to the protection scope of the technical solution of the present disclosure.

What is claimed is:

1. A paramyxovirus vaccine strain for novel coronavirus pneumonia, wherein the paramyxovirus vaccine strain for novel coronavirus pneumonia is a recombinant paramyxovirus strain that expresses the novel coronavirus S1 protein (rCNDV-S), with an access number CCTCC NO: V202119, deposited in China Center for Type Culture Collection, Wuhan University, Wuhan, China.

2. A vaccine composition, comprising a pharmaceutically effective amount of the paramyxovirus vaccine strain for novel coronavirus pneumonia according to claim 1 and a pharmaceutically acceptable adjuvant.

3. The vaccine composition according to claim 2, wherein the pharmaceutically acceptable adjuvant is one or more selected from the group consisting of propolis, liposomes, lentinan, *ganoderma* polysaccharide, *astragalus* polysaccharide, *gastrodia* extract, *cordyceps* extract, *Sophora flavescens* extract, and levamisole.

* * * * *